US005650447A

United States Patent [19]
Keefer et al.

[11] Patent Number: 5,650,447
[45] Date of Patent: Jul. 22, 1997

[54] NITRIC OXIDE-RELEASING POLYMERS TO TREAT RESTENOSIS AND RELATED DISORDERS

[75] Inventors: Larry K. Keefer, Bethesda, Md.; Thomas C. Hutsell, North Oaks, Minn.

[73] Assignees: The United States of America as represented by the Secretary of the Department of Health and Human Services, Washington, D.C.; Comedicus, Incorporated, Long Lake, Minn.

[21] Appl. No.: 214,372

[22] Filed: Mar. 17, 1994

Related U.S. Application Data

[63] Continuation-in-part of Ser. No. 121,169, Sep. 14, 1993, Pat. No. 5,525,357, which is a continuation-in-part of Ser. No. 935,565, Aug. 24, 1992, Pat. No. 5,405,919.

[51] Int. Cl.$^6$ .............................. A01N 33/26; A61K 47/30
[52] U.S. Cl. .................... 514/772.4; 514/772.6; 514/773; 514/784; 514/785; 514/788; 514/611
[58] Field of Search .............. 514/772.1, 772.2, 514/772.3, 772.4, 772.5, 772.6, 773, 784, 785, 788; 424/78.08

[56] References Cited

U.S. PATENT DOCUMENTS

| | | | |
|---|---|---|---|
| 3,880,822 | 4/1975 | Perrotti et al. | 525/340 |
| 4,954,526 | 9/1990 | Keefer et al. | 514/611 |
| 5,039,705 | 8/1991 | Keefer et al. | 514/611 |
| 5,155,137 | 10/1992 | Keefer et al. | 514/611 |
| 5,185,376 | 2/1993 | Diodati et al. | 514/611 |
| 5,208,233 | 5/1993 | Keefer et al. | 514/231.8 |
| 5,212,204 | 5/1993 | Keefer et al. | 514/647 |
| 5,219,710 | 6/1993 | Horn et al. | 526/311 |
| 5,250,550 | 10/1993 | Keefer et al. | 514/357 |

OTHER PUBLICATIONS

Abrams, "Mechanisms of Action of the Organic Nitrates in the Treatment of Myocardial Ischemia," *Amer. J. Cardiology*, 70:30B–41B (1992).

Clowes et al., "Kinetics of Cellular Proliferation After Arterial Injury," *Lab. Invest.*, 49(3):327–333 (1983).

Clowes et al., "Mechanisms of Stenosis After Arterial Injury," *Lab. Invest.*, 49(2):208–215 (1983).

Diodati et al., "Complexes of Nitric Oxide with Nucleophiles as Agents for the Controlled Biological Release of Nitric Oxide: Antiplatelet Effect," *Thrombosis and Haemostasis*, 70(4):654–658 (1993).

Diodati et al., "Complexes of Nitric with Nucleophiles as Agents for the Controlled Biological Release of Nitric Oxide: Hemodynamic Effect in the Rabbit," *J. Cardiovasc. Pharmacol.*, 22:287–292 (1993).

Feldman et al., "The Suprising Life of Nitric Oxide," *C&EN*:26–38 (Dec. 20, 1993).

Ferns et al., "Inhibition of Neointimal Smooth Muscle Accumulation After Angioplasty by an Antibody to PDGF," *Science*, 253:1129–1132 (1991).

Forrester et al., "A Paradigm for Restenosis Based on Cell Biology: Clues for the Development of New Preventive Therapies," *JACC*, 17(3):758–769 (1991).

(List continued on next page.)

*Primary Examiner*—Peter F. Kulkosky
*Attorney, Agent, or Firm*—Leydig, Voit & Mayer, Ltd.

[57] ABSTRACT

Methods of amelioration, treatment and prevention for restenosis and related disorders are provided. Methods involve the administration of nitric oxide by a nitric oxide delivery means comprising a restenosis-ameliorating or therapeutically/prophylactically effective amount of either a polymer to which is bound a nitric oxide-releasing $N_2O_2^-$ functional group a compound comprising a nitric oxide-releasing $N_2O_2^-$ functional group. Also provided are nitric oxide delivery means comprising such nitric oxide-releasing polymers or compounds for use in such methods. Preferably, the delivery means is coated with a nitric oxide-releasing polymer, which may be biodegradable, and enables the controllable and predictable release of NO to a given site in such a manner that effective ameliorating, prophylactic or therapeutic dosing is realized.

42 Claims, 7 Drawing Sheets

OTHER PUBLICATIONS

Golino et al., "Endothelium–Derived Relaxing Factor Modulates Platelet Aggregation in an In Vivo Model of Recurrent Platelet Activation," *Circ. Res.*, 71(6):1447–1456 (1992).

Groves et al., "Exogenous Nitric Oxide Inhibits In Vivo Platelet Adhesion Following Balloon Angioplasty," *Cradiovasc. Res.*, 26:615–619 (1992).

Groves et al., "SIN–1 Reduces Platelet Adhesion and Platelet Thrombus Formation in a Porcine Model of Balloon Angioplasty," *Circ.*, 87(2):590–597 (1993).

Hadoke et al., "Characterization of the Responses of Isolated Rings of Rabbit Left Carotid Artery, A Potential Protocol for the Assessment of Pathologically Induced Functional Changes," *JPM*, 29(4):195–202 (1993).

Harrison, "Endothelial Modulation of Vascular Tone: Relevance to Coronary Angioplasty and Restenosis," *JACC*, 17(6):71B–76B (1991).

Ip et al., "The Role of Platelets, Thrombin and Hyperplasia in Resenosis After Coronary Angioplasty," *JACC*, 17(6):77B–88B (1991).

Just et al., "Effect of Molsidomine on Thrombus Formation in Stenosed Coronary Arteries of Dogs and Pigs," *J. Cardiovasc. Pharmacol.*, 14(Suppl. 11):S129–S136 (1989).

Lindner et al., "Proliferation of Smooth Muscle Cells After Vascular Injury is Inhibited by an Antibody Against Basic Fibroblast Growth Factor," *PNAS USA*, 88:3739–3743 (1991).

Liu et al., "Restenosis After Coronary Angioplasty, Potential Biologic Determinants and Role of Intimal Hyperplasia," *Circulation*, 79(6):1374–1387 (1989).

McNamara et al., "L–Arginine Inhibits Balloon Catheter–Induced Intimal Hyperplasia," *Biochem. and Biophys. Res. Comm.*, 193(1):291–296 (1993).

Ovize et al., "Inhibition of Coronary Artery Thrombosis by SIN–1, a Donor of Nitric Oxide," *J. Cardiovasc. Pharmacol.*, 16:641–645 (1990).

Reden, J., "Molsidomine," *Blood Vessels*, 27:282–294 (1990).

Schwartz et al., "The Restenosis Paradigm Revisited: An Alternative Proposal for Cellular Mechanisms," *JACC*, 20(5):1284–1293 (1992).

Search Report—Bibliographic Citation List Generated by Medlars II regarding Molsidomine.

Search Report—Bibliographic Citation List Generated by Medlars II regarding Linsidomine.

Search Report—Bibliographic Citation List Generated by Medlars II regarding Faxon D.

Search Report regarding Molsidomine or Linsidomine.

Search Report regarding Restensosis or Angioplasty and Nitric Oxide or Nitric Oxide–Releasing Compound.

Article—Nitric–Oxide Boosters May Fight Off PTCA Restenosis.

Mascarenhas Dissertation Abstracts pp. 54–94 Dec. 1993.

Abstract of Soviet Union 537599 Nov. 1977.

5,650,447

NITRIC OXIDE-RELEASING POLYMERS TO TREAT RESTENOSIS AND RELATED DISORDERS

This application is a continuation-in-part of U.S. patent application Ser. No. 08/121,169, filed Sep. 14, 1993, now U.S. Pat. No. 5,525,357 which, in turn, is a continuation-in-part of U.S. application Ser. No. 07/935,565, filed Aug. 24, 1992 now U.S. Pat. No. 5,405,919. The entire disclosures of the '169 application and the '919 patents are incorporated herein by reference.

TECHNICAL FIELD OF THE INVENTION

The present invention relates to a method of using nitric oxide-releasing agents and polymers to treat, ameliorate or prevent the onset of restenosis and related disorders. The present invention also relates to nitric oxide delivery means comprising nitric oxide-releasing agents or polymers for use in the method.

BACKGROUND OF THE INVENTION

Over half a million interventional intravascular procedures are performed each year. While such invasive procedures continue to improve over time, as many as 30–50% of the procedures performed each year fail as a result of restenosis. The reduction of restenosis is, therefore, often cited as the most critical factor in increasing the success realized in the treatment of cardiovascular disease through the use of interventional intravascular procedures, such as angioplasty, atherectomy, and procedures utilizing stents and laser technology.

In balloon angioplasty, for example, a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using x-ray visualization. The deflated balloon is advanced until it reaches the site of the luminal narrowing, at which point the physician inflates the balloon one or more times to a pressure of about 4–6 atm for about 60 sec. When inflated, the balloon cracks and fractures the plaque and stretches the muscle fiber in the artery wall beyond its ability to recoil completely. Although no plaque is removed in this procedure, the fracturing of the plaque and the stretching of the arterial wall increase the vessel lumen, thereby allowing for increased blood flow through the lumen.

The restenosis that accompanies such procedures is characterized by platelet aggregation and adhesion, smooth muscle cell proliferation, narrowing of the vessel lumen, restricted vasodilation, and an increase in blood pressure. Smooth muscle cells in the intimal layer of the artery have been reported to enter the growth cycle within about 2–3 days of these procedures and to proliferate for several days thereafter (intimal hyperplasia), the vast majority of smooth muscle cell proliferation reportedly being completed within 7 days (Stemerman, *Am. J. Pathol.* 73: 7–18 (1973)). Attempts have been made to provide nitric oxide as a means of treating platelet aggregation and the like.

Nitric oxide in its pure form, however, is a highly reactive gas having limited solubility in aqueous media (WHO Task Group on Environmental Health Criteria for Oxides of Nitrogen, *Oxides of Nitrogen*, Environmental Health Criteria 4 (World Health Organization: Geneva, 1977)). Nitric oxide, therefore, is difficult to introduce reliably into most biological systems without premature decomposition.

A number of compounds have been developed which are capable of delivering nitric oxide, including compounds which release nitric oxide upon being metabolized and compounds which release nitric oxide spontaneously in aqueous solution.

Those compounds which release nitric oxide upon being metabolized include the widely used nitrovasodilators glyceryl trinitrate and sodium nitroprusside (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)), which are relatively stable but release nitric oxide on activation. While this feature may be an advantage in some applications, it also can be a significant liability. For example, tolerance to glyceryl trinitrate can develop via the exhaustion of the relevant enzyme/cofactor system (Ignarro et al., *Annu. Rev. Pharmacol. Toxicol.*, 25, 171–191 (1985); Kuhn et al., *J. Cardiovasc. Pharmacol.*, 14 (Suppl. 11), S47–S54 (1989)). Also, prolonged administration of nitroprusside results in the metabolic production of cyanide, which leads to toxicity (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369). S-Nitroso-N-acetylpenicillamine has been reported to release nitric oxide in solution and to be effective at inhibiting DNA synthesis (Garg et al., *Biochem. and Biophys. Res. Comm.*, 171, 474–479 (1990)).

Numerous nitric oxide-nucleophile complexes have been described, e.g., Drago, *ACS Adv. Chem. Ser.*, 36, 143–149 (1962). See also Longhi and Drago, *Inorg. Chem.*, 2, 85 (1963). Some of these complexes are known to evolve nitric oxide on heating or hydrolysis, e.g., Maragos et al., *J. Med. Chem.*, 34, 3242–3247 (1991).

A very important class of such agents is the just-named nitric oxide-nucleophile complexes (NONOates). Recently, a method for treating cardiovascular disorders in a mammal with certain nitric oxide-nucleophile complexes was disclosed, e.g. in U.S. Pat. No. 4,954,526. These compounds contain the anionic $N_2O_2^-$ group or derivatives thereof. See also, Maragos et al., supra. Many of these compounds have proven especially promising pharmacologically because, unlike nitrovasodilators such as nitroprusside and nitroglycerin, they release nitric oxide without first having to be activated. The only other series of drugs currently known to be capable of releasing nitric oxide purely spontaneously is the S-nitrosothiol series, compounds of structure R—S—NO (Stamler et al., *Proc. Natl. Acad. Sci. U.S.A.*, 89, 444–448 (1992)); however, the R—S—NO→NO reaction is kinetically complicated and difficult to control (Morley et al., *J. Cardiovasc. Pharmacol.*, 21, 670–676 (1993)). Similarly, compounds like molsidomine and linsidomine not only require activation to release NO, but they also release undesirable free radicals. The NONOates, therefore, are thus unique among currently known drugs in that they decompose at any given pH by a first-order reaction to provide doses of nitric oxide that can be predicted, quantified, and controlled. See, e.g., Maragos et al., supra.

Nitric oxide/nucleophile complexes which release nitric oxide in aqueous solution are also disclosed in U.S. Pat. Nos. 5,039,705, 5,155,137, 5,185,376, 5,208,233, 5,212,204, 5,250,550, 5,366,977 and 5,389,675, as being useful cardiovascular agents (see also Maragos et al., *J. Med. Chem.*, 34, 3242–3247 (1991)).

Despite the promise of the nitric oxide/nucleophile adducts that have been investigated, their pharmacological application has been limited by their tendency to distribute evenly throughout the medium. Such even distribution is a great advantage in many research applications, but tends to compromise their selectivity of action. Another limitation to the application of these nitric oxide/nucleophile adducts is their propensity for relatively rapid release of nitric oxide, which may necessitate frequent dosing to achieve a prolonged biological effect. The nitric oxide-releasing polymers of the present invention overcome these limitations by enabling concentrated and localized release of NO at a given site in a controllable and predictable manner such that effective dosing may be realized.

There remains a need, however, for an effective method of preventing, ameliorating and treating restenosis. Accordingly, the present invention provides a method of prevention, amelioration and treatment for restenosis and related disorders which overcomes the disadvantages of currently available treatment methods, and delivery means for use in the prevention, amelioration and treatment of restenosis and related disorders. These and other objects and advantages of the present invention, as well as additional inventive features, will be apparent from the description of the invention provided herein.

SUMMARY OF THE INVENTION

The present invention provides methods of preventing, alleviating, ameliorating and treating restenosis and related disorders comprising the administration of a delivery means comprising a nitric oxide-releasing agent, such as a compound comprising a nitric oxide-releasing $N_2O_2^-$ functional group or a polymer to which is bound a nitric oxide-releasing $N_2O_2^-$ functional group, in an amount sufficient to release a restenosis-ameliorating or prophylactically or therapeutically effective amount of nitric oxide. The method of treatment involves the administration of the delivery means comprising a nitric oxide-releasing agent after the onset of signs of restenosis or a related disorder, whereas the method of prevention involves the administration of the delivery means comprising a nitric oxide-releasing agent prior to the onset of signs of restenosis or a related disorder. Preferably, the delivery means is coated with or made of a nitric oxide-releasing polymer and enables the controllable and predictable localized release of NO to a given site in such a manner that effective restenosis-ameliorating or prophylactic or therapeutic dosing is realized. The delivery means may be biodegradable. Delivery means comprising the nitric oxide-releasing agent are also provided.

BRIEF DESCRIPTION OF THE DRAWINGS

FIG. 8 is a graph of platelets deposited ($\times 10^{-9}$) at a thrombogenic site (Dacron graft) in an A-V shunt in baboons versus time of exposure (min) to

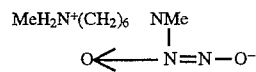

Figure 1:
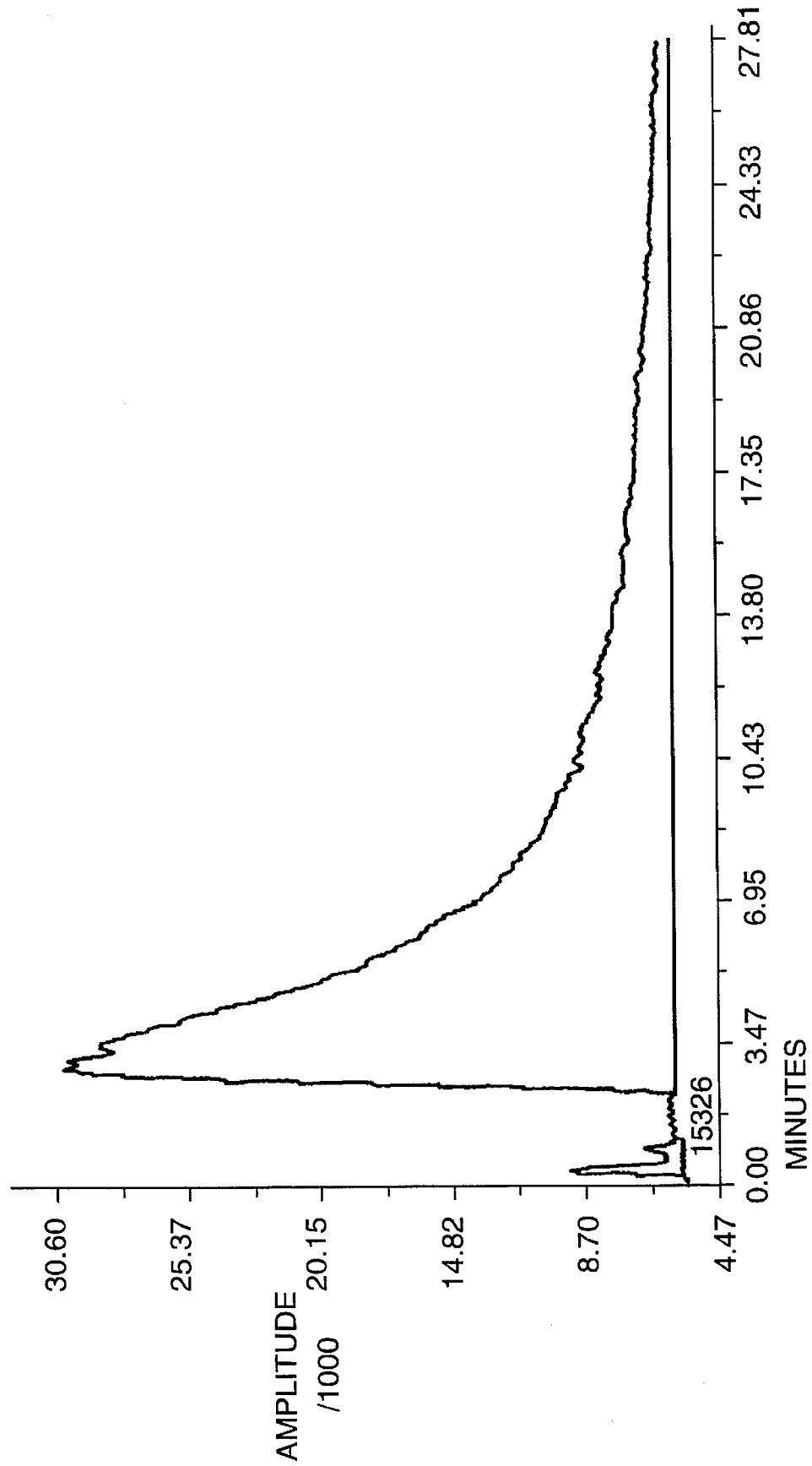
FIG. 1 is the chemiluminescence detector response to nitric oxide generated from the polymer-bound nitric oxide-releasing $N_2O_2^-$ functional group composition of Example 3 in accordance with the invention.

(MAHMA/NO).

DETAILED DESCRIPTION OF THE INVENTION

The present invention provides methods for the prophylactic, ameliorating and therapeutic treatment of restenosis and related disorders in a mammal. Alleviation of the restenosis may also be achieved. The prophylactic method involves the administration to a mammal, in particular a human, of nitric oxide by a nitric oxide delivery means comprising a prophylactically effective amount of a nitric oxide-releasing agent, such as a compound comprising a nitric oxide-releasing $N_2O_2^-$ functional group or a polymer to which is bound a nitric oxide-releasing $N_2O_2^-$ functional group, capable of locally releasing nitric oxide to a site at risk for restenosis or a related disorder in the mammal. The ameliorating or therapeutic method involves the administration of nitric oxide by a nitric oxide delivery means comprising a therapeutically effective amount of the nitric oxide-releasing agent to a site already affected by restenosis or a related disorder in the mammal. Related disorders refers to conditions wherein the vasculature is affected by one or more of the following: platelet aggregation, platelet adhesion, smooth muscle cell proliferation, vasoconstriction, and/or increased blood pressure, whether the result of physical or chemical injury or disease. Localized release means release at or near the site at risk for or affected by restenosis or related disorder, irrespective of the actual route of administration employed. Nitric oxide delivery means encompasses the many forms in which the nitric oxide-releasing agent may be administered, such as vascular graft prosthetic implant, stent, heart valve, suture, drug pump, catheter, self-adhering means, liposome, microparticle, microsphere, bead, and disk as described more fully below.

Restenosis-ameliorating and prophylactically and therapeutically effective amounts are as described below with respect to dosages. Whether or not a particular mammal is at risk for restenosis or a related disorder may be determined by methods well-known to those of ordinary skill in the art. Factors such as gender, previous medical history, e.g., diabetes mellitus, smoking, unstable or variant angina pectoris, hypercholesterolemia and previous myocardial infarct, would be expected to place an individual at higher risk. Similarly, whether or not a particular mammal is affected by restenosis or a related disorder may be determined by methods known in the art, such as coronary angiography. The characterization of the restenosis may include the determination of the number and type of vessel(s) affected, portion of vessel affected, i.e., proximal or distal, and the complexity of the stenosis, e.g., length, degree of occlusion, eccentricity of lesion, ostial lesions, and degree of calcification. The present invention also provides various nitric oxide delivery means for use in the present prophylactic, restenosis-ameliorating and therapeutic methods as described more fully below.

The present invention is predicated on the discovery that useful pharmacological agents can be provided by incorporating nitric oxide-releasing $N_2O_2^-$ functional groups into a polymeric matrix. Accordingly, the $N_2O_2^-$ functional group is "bound to the polymer" as that term has been defined herein. It has been discovered that incorporation of the $N_2O_2^-$ functional group into a polymeric matrix provides a polymer-bound nitric oxide/nucleophile adduct composition that can be administered for localized release of NO to a biological site of interest. Site-specific delivery of the polymer-bound adduct composition enhances the selectivity of action of the nitric oxide-releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue, such as an antibody to fibrin or tissue thromboplastin. Similarly, attachment of $N_2O_2^-$ groups to small peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O_2^-$ functional group into a polymeric matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

While not being bound to any particular theory, it is believed that longevity of nitric oxide release in the polymer-bound nitric oxide/nucleophile adduct compositions of the present invention is to be attributed both to the physical structure of the composition and to electrostatic effects. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the half-life of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$– catalyzed decomposition (Hrabie et al., *J. Org. Chem.*, 58, 1472–1476 (1993)).

The nitric oxide-releasing $N_2O_2^-$ functional groups that are bound to the polymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing $X[N(O)NO]^-$ group in the vicinity of the particular cells of interest. As an example, covalent attachment of a protecting group to the anionic $[N(O)NO]^-$ function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/nucleophile complex can be targeted to maximize the desired effect. While the polymer-bound nitric oxide releasing compositions of the present invention are capable of releasing nitric oxide in an aqueous solution, such a polymer preferably releases nitric oxide under physiological conditions.

The nitric oxide releasing $N_2O_2^-$ functional group is preferably a nitric oxide/nucleophile adduct, i.e., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of a primary amine (e.g., $X=(CH_3)_2CHNH$, as in $(CH_3)_2CHNH[N(O)NO]Na$), a secondary amine (e.g., $X=(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, X=(ethylamino) ethylamine, as in the zwitterion $CH_3CH_2N[N(O)NO]^-CH_2CH_2NH_3^+$, or X=3–(n-propylamino)propylamine, as in the zwitterion $CH_3CH_2CH_2N[N(O)NO]^{-CH_2}CH_2CH_2NH_3^+)$, or oxide (i.e., $X=O^-$, as in $NaO[N(O)NO]Na$), or a derivative thereof. Such nitric oxide/nucleophile complexes are stable solids and are capable of delivering nitric oxide in a biologically usable form at a predictable rate.

The nucleophile residue is preferably not an entity such as that of sulfite (e.g., $X=SO_3^-$, as in $NH_4O_3S[N(O)NO]NH_4$) even though the complex is a stable compound, since it is capable of releasing nitric oxide in an aqueous environment only under harsh, nonphysiological conditions.

Other suitable nitric oxide/nucleophile complexes include those having the following formulas:

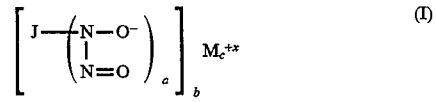  (I)

wherein J is an organic or inorganic moiety, including, for example, a moiety which is not linked to the nitrogen of the $N_2O_2^-$ group through a carbon atom, $M^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described in U.S. Pat. No. 5,212,204, incorporated herein by reference;

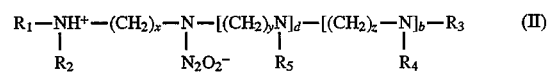  (II)

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described in U.S. Pat. No. 5,155,137, incorporated herein by reference;

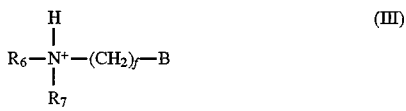

wherein B is

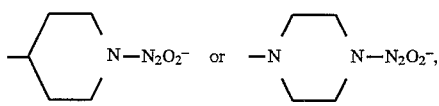

$R_6$ and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

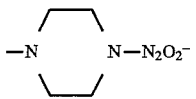

then f is an integer from 2 to 12, as described in U.S. Pat. No. 5,250,550 incorporated herein by reference;

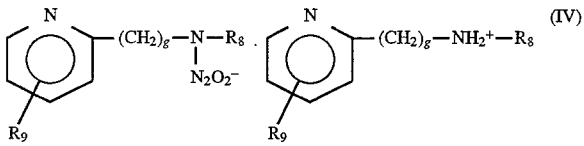

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$–$C_{12}$ straight or branched chain alkyl, and g is 2 to 6, as described in U.S. Pat. No. 5,250,550, incorporated herein by reference;

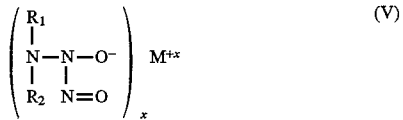

wherein $R_1$ and $R_2$ are independently selected from the group consisting of a straight chain or branched chain $C_1$–$C_{12}$ alkyl group and a benzyl group, preferably such that no branch occurs on the alpha carbon atom, or else $R_1$ and $R_2$, together with the nitrogen atom, are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. Nos. 5,039,705 and 5,208,233 and U.S. patent application Ser. No. 08/017,270, filed Feb. 12, 1993, and incorporated herein by reference;

$$K[(M)_{x'}(L)_y(R^1R^2N-N_2O_2)_z] \quad (VI)$$

wherein M is a pharmaceutically acceptable metal, or, where x is at least two, a mixture of two different pharmaceutically acceptable metals, L is a ligand different from ($R^1R^2N-N_2O_2$) and is bound to at least one metal, $R^1$ and $R^2$ are each organic moieties and may be the same or different (preferably where M is copper, x is one, L is methanol, and y is one, that at least one of $R^1$ or $R^2$ is not ethyl), x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. Pat. No. 5,389,675 and incorporated herein by reference;

$$[R-N(H)N(NO)O-]_yX \quad (VII)$$

wherein R is $C_{2-8}$ lower alkyl, phenyl, benzyl, or $C_{3-8}$ cycoloalkyl, any of which R groups may be substituted by one to three substituents, which are the same or different, selected from the group consisting of halo, hydroxy, $C_{1-8}$ alkoxy, $-NH_2$, $-C(O)NH_2$, $-CH(O)$, $-C(O)OH$, and $-NO_2$, X is a pharmaceutically acceptable cation, a pharmaceutically acceptable metal center, or a pharmaceutically acceptable organic group selected from the group consisting of $C_{1-8}$ lower alkyl, $-C(O)CH_3$, and $-C(O)NH_2$, and y is one to three, consistent with the valence of X, as described in U.S. Pat. No. 4,954,526 and incorporated herein by reference; and

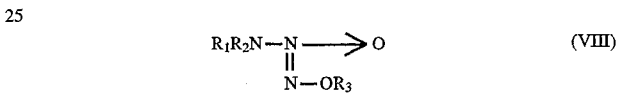

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$, together with the nitrogen atom to which they are bonded, form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula $-(CH_2)_n-ON=N(O)NR_1R_2$, wherein n is an integer of 2–8, and $R_1$ and $R_2$ are as defined above; preferably $R_1$, $R_2$ and $R_3$ do not contain a halo or a hydroxy substituent α to a heteroatom, as described in U.S. Pat. No. 5,366,977.

Any of a wide variety of polymers can be used in the context of the present invention. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, and polyvinylchloride; polyethylenimine or derivatives thereof; polyethers, such as polyethyleneglycol; polyesters, such as poly(lactide/glycolide); polyamides, such as nylon; polyurethanes; colestipol and derivatives thereof; biopolymers, such as peptides, proteins, oligonucleotides, nucleic acids, starburst dendrimers, and the like, and macromolecules, such as antibodies.

The physical and structural characteristics of the polymers suitable for use in the present invention are not narrowly critical, but rather will depend on the end use application. It will be appreciated by those skilled in the art that, where the polymer-bound nitric oxide/nucleophile adduct compositions of the present invention are intended for local or relatively short term administration, they need not be biodegradable. For some uses, such as post-angioplasty coronary bypass surgery or for intimal hyperplasia associated with vascular graft implants or the like, it may be desirable that the polymer of the polymer-bound compositions slowly dissolve in a physiological environment.

The polymer-bound nitric oxide releasing agents may be administered in a wide variety of forms of delivery means. Any delivery means should adequately protect the integrity of the nitric oxide prior to its release and should control the release of the nitric oxide at such a rate, in such an amount, and in such a location as to serve as an effective means of preventing or treating restenosis. For example, delivery means for local administration or administration for localized release include, but are not limited to, sutures, vascular implants (e.g., endoluminal or periadventitial), stents, heart valves, drug pumps, drug-delivery catheters (pressure-driven, iontophoretic), self-adhering means (vessel coatings) such as endoluminal implants, liposomes, microparticles, microspheres, beads, disks or other devices. The advantages of local administration or release include the ability to attain effective concentrations of drug at the target site more quickly, the use of a smaller dose, and the realization of fewer toxic side effects than systemic administration and release. Delivery means for systemic administration for localized release include, but are not limited to, solutions, suspensions, emulsions, capsules, stables, tablets, dermal (topical) patches, lozenges, aerosols, liposomes, microparticles, microspheres, beads, prodrugs, such as a cholesterol avid prodrug, for release into a vascular lesion, tissue-specific antibodies, such as antibodies to fibrin or tissue thromboplastin, small peptides that mimic ligand recognition sequences, and sequence-specific oligonucleotides as described above. The polymer, itself, may be structurally sufficient to serve as a form of delivery means. Alternatively, the polymer-bound composition may be incorporated into or coated onto other matrices, substrates or the like, or it may be microencapsulated, or the like.

The nitric oxide-releasing complexes having $N_2O_2^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent. Monomers containing the $N_2O_2^-$ group also may be dissolved in molten polymer which, upon solidification when the temperature is lowered, contains a rather uniform distribution of $N_2O_2^-$ groups within the matrix.

Alternatively, nitric oxide-releasing $N_2O_2^-$ functional groups may be bound to the polymer by formation of a nitric oxide/nucleophile complex of the types and having the formulas of those described above, in situ on the polymer. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release. For example, where the polymer is polyethylenimine, the polymer includes nucleophilic nitrogen atoms which react with nitric oxide to form the $N_2O_2^-$ functional group at the nitrogen in the backbone. Where the $N_2O_2^-$ functional group is a group pendant to the polymer backbone, the polymer contains, or is derivatized with, a suitable nucleophilic residue capable of reacting with nitric oxide to form the $N_2O_2^-$ functionality. Reaction of the polymer which contains a suitable nucleophilic residue, or of the suitably derivatized polymer, with nitric oxide thus provides a polymer-bound nitric oxide-releasing $N_2O_2^-$ functional group. To form the polymer-bound nitric oxide releasing $N_2O_2^-$ functional group, a net positive charge is imparted to the polymer near the site on the polymer where the $N_2O_2^-$ functional group is formed.

One skilled in the art will appreciate that suitable methods of administering the nitric oxide-releasing agents of the present invention to an animal are available, and, although more than one route can be used to administer a particular composition, a particular route can provide a more immediate and more effective reaction than another route. Pharmaceutically acceptable carriers are also well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The biodegradable nitric oxide-releasing agents of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a restenosis-ameliorating or prophylactic or therapeutic response in the animal over a reasonable time frame. The dose will be determined by the strength of the particular nitric oxide-releasing agent employed, the type of delivery means employed, the route of administration, the condition and weight of the animal to be treated, the timing of administration, i.e., prior to the onset of restenosis or related disorder or after the onset of restenosis or related disorder, and the length of time of administration. The size of the dose also will be determined by the existence, nature, and extent of any adverse side-effects that might accompany the administration of a particular composition. A suitable dose, for example, is about 0.05 mg–100 mg of nitric oxide. The dose may be administered acutely or chronically as dictated by the condition being treated, ameliorated or prevented.

The following examples further illustrate the present invention, but do not limit the scope thereof.

In the Examples, chemiluminescence analysis for total recoverable nitric oxide from polymers containing the nitric oxide-releasing $N_2O_2^-$ functional group by acid treatment was carried out as follows:

The analysis of NO adducts, i.e., polymers containing the nitric oxide-releasing $N_2O_2^-$ functional group, was done on a nitric oxide analyzer and was patterned after the procedure of Maragos et al., *J. Med. Chem.*, 34, 3242–3247 (1991). A reactor vessel fitted with a septum was charged with a small aliquot of the polymer to be studied and the system was purged with helium for several minutes to remove traces of oxygen. Two milliliters of 10 mM sulfuric acid was added by injection through the septum to begin reaction. Gaseous effluent was swept continuously via a fritted glass bubbler positioned at the bottom of the reactor vessel (i.e., immersed in the acid solution) into a chemiluminescence detector (Thermal Energy Analyzer Model 502LC, Thermedics, Inc., Woburn, Mass.). The area of the resulting chemiluminescence signal versus time curve was electronically computed and compared with that of a known quantity of nitric oxide gas standard to determine the amount of nitric oxide produced by acid treatment of the polymer aliquot.

This procedure was used to estimate the total amount of nitric oxide recoverable from the polymer. To estimate the rate of nitric oxide generation under physiological conditions, the inventive polymers were subjected to a procedure identical to that described above, except that 2 ml of 10 mM phosphate buffer, pH 7.4, was injected into the reactor vessel in place of the sulfuric acid solution to start the reaction.

EXAMPLES

Example 1

This example illustrates the preparation of a polymer-bound nitric oxide/nucleophile complex by coprecipitation of a monomeric form thereof with a polymer.

One gram of polymer [poly(lactide/glycolide, 50:50) from MediSorb] was dissolved in 2 ml of tetrahydrofuran. To the solution was added 300 mg of DETA/NO, $[H_2N(CH_2)_2]_2N$—$N_2O_2H$, zwitterionic form, and the mixture was stirred under an argon stream to remove solvent slowly until the mixture became too viscous to stir. The mixture was then placed in a vacuum oven (ca. 1 mm) at 30° C. for 5 hours to remove the residual solvent. The mixture was finally pressed on a carver press at 20,000 lbs. at 140° F. for 5 minutes. A 1"×1" film, 44 mils thick, was thus prepared. Using the chemiluminescence procedure described above, nitric oxide was recovered from this polymer on treatment with acid at the rate of 8 nmol of NO per milligram of solid.

Example 2

This example illustrates the preparation of a polymer-bound nitric oxide/nucleophile adduct in which the $N_2O_2^-$ functional group is bound directly to an atom in the polymer backbone.

A slurry of 10.0 g of polyethylenimine on silica gel (Aldrich) in 150 ml of acetonitrile was stirred for 3 days under a nitric oxide pressure of 5 atm or 75–80 psig. The resulting orange solid was filtered, washed with acetonitrile and then ether, and dried in vacuo for 6 h. Using the chemiluminescence procedure described above, it was determined that nitric oxide was recovered from this polymer on treatment with acid at the rate of 3 nmol/mg.

Control experiments with polymer that had not been exposed to NO produced no chemiluminescence signal.

Example 3

This example illustrates the preparation of a polymer containing nitric oxide-releasing $N_2O_2^-$ groups that are attached to nucleophile residues pendant on the polymer backbone by the reaction of a primary amine with a derivatized polystyrene.

An aminostyrene polymer was prepared by warming 3.0 g of chloromethylated polystyrene (1% divinylbenzene; 1.09 mEq Cl per gram; 200–400 mesh; Polysciences, Inc., Warrington, Pa.) in 20 ml of n-propyl-1,3-propanediamine to 60° C. in an oil bath and swirling periodically for 5 days. The polymer was then filtered, washed repeatedly with water, then methanol and finally dichloromethane, and dried in vacuo for 24 h. Elemental analysis showed this material to be 2.21% nitrogen; indicating that approximately 80% of the chlorines had been replaced by propylpropanediamino groups.

A slurry of 1.0 g of the aminopolystyrene polymer in 50 ml of acetonitrile was placed under 5 atm of nitric oxide in a Parr apparatus and shaken intermittently for 3 days. The product was filtered and dried in vacuo to yield 0.84 g of cream colored polymer. The elemental analysis (c: 87.32; H: 8.00; N: 2.45) revealed that approximately one-third of the amino side chains became attached to $N_2O_2^-$ groups under these conditions.

Using the chemiluminescence procedure described above, it was demonstrated that nitric oxide can be recovered from $N_2O_2^-$ group-containing polymer prepared as described above. The observed chemiluminescence detector response as a function of time and the amount of nitric oxide regenerated when the polymer was treated with acid are illustrated in FIG. 1. As can be seen, only small amounts of nitric oxide were evolved from the solid, itself, but when 2 ml of 10 mM sulfuric acid was injected via a septum, a sudden pulse of nitric oxide appeared. Integration of this apparently first-order generation of nitric oxide over time indicated that 11 nmol of nitric oxide was recovered from 1 mg of polymer.

The reaction was repeated using 10 mM phosphate buffer at pH 7.4 in place of the sulfonic acid to verify the slow release of nitric oxide at physiological pH. The chemiluminescence detector showed that nitric oxide was generated from this polymer much more slowly.

Example 4

This example illustrates the preparation of a polyethylene glycol-based NO-releasing polymer using two different methods of preparation.

In one method, 20 mg of 1,1-diethyl-2-hydroxy-2-nitrosohydrazine sodium salt (DEA/NO) and 2.5 g of polyethyleneglycol-1450 (Union Carbide) were dissolved in 25 ml of methanol. The homogenous solution was placed on a rotary evaporator at 40° C. and the solvent was removed under vacuum to give a uniform solid solution. The sample was stored in a clear glass vial, under ordinary laboratory lighting, at ambient temperature and atmosphere. The stability of the formulation was followed over a period of seven days. The measurements were carried out by monitoring the absorbance of the polymer at the 250 nm peak in the electronic spectrum. No changes in the absorbance were observed in this time period.

In a second method, 2.5 g of polyethylene glycol-1450 was heated to 46° C. until completely melted. To the liquid polyethylene glycol was added 36 mg (0.232 mmol) of DEA/NO and the container was placed on a vortex mixer. A homogeneous solution was attained that gradually solidified upon cooling to ambient temperature. The stability of the solution was monitored as described above. No change in the absorbance for the 250 nm chromophore was observed at seven weeks of storage.

Example 5

This example illustrates the preparation of a polymer composed of a polyamine/nitric oxide complex N-[4-[1-(3-aminopropyl)-2-hydroxy-2-nitrosohydrazino)butyl]-1,3-propanediamine, zwitterionic form (SPER/NO); and polyethylene glycol.

A 1.2% (w/w) solution of KOH in polyethylene glycol-1450 (Union Carbide) was prepared in aqueous medium, and evaporated to dryness under vacuum (PEG-KOH). To 1.144 g of molten PEG-KOH was added 11.65 mg (0.042 mmol) of SPER/NO and the resulting mixture was blended to a uniform mass. No decrease was observed in the absorbance after five weeks of storage at room temperature in a clear glass vial.

PHARMACOLOGY EXPERIMENT

In the test procedures utilized, thoracic aortic rings from New Zealand White rabbits were suspended in pH 7.4 buffer at 37° C. and a 10 g preload was applied to each. After equilibration for 2 hours, the rings were preconstricted with norepinephrine. The percent relaxation caused by adding the polymer-bound compositions of the present invention to the organ baths at successively increasing concentrations was measured. See Maragos et al., *J. Med. Chem.*, 34, 3243–3247 (1991).

Figure 2:
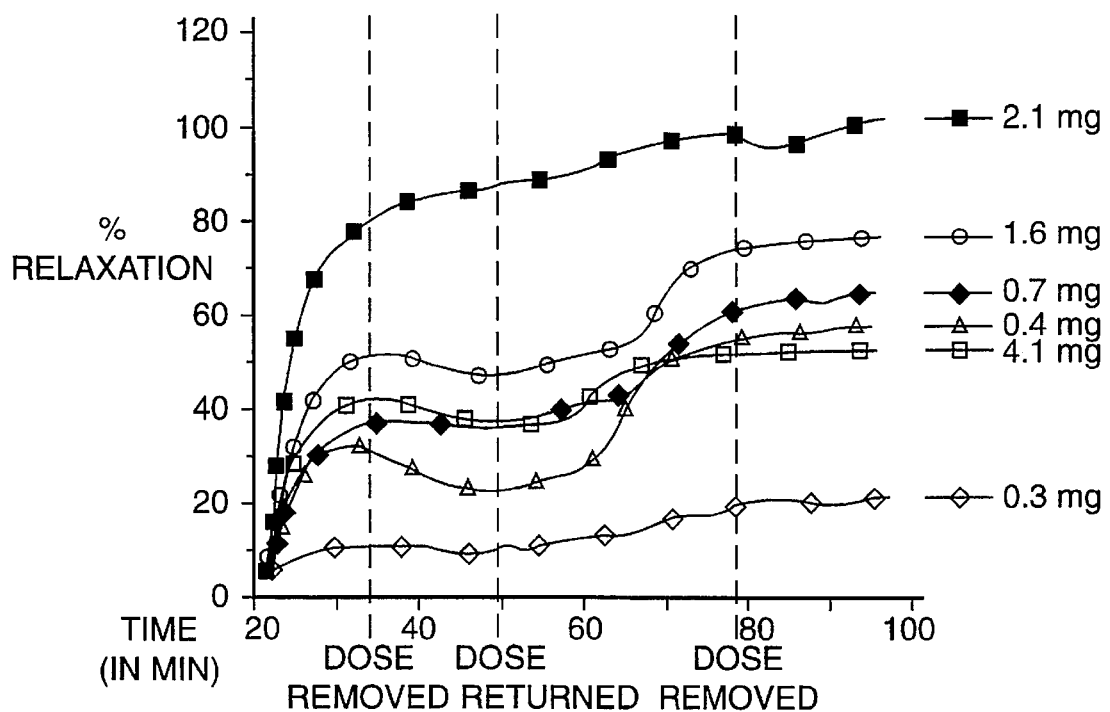
FIG. 2 is a graph illustrating the time course of vascular relaxation with different doses of the polymer-bound nitric oxide-releasing composition of Example 1.

A polymer film as described in Example 1 was cooled on dry ice and a small piece was sliced off. This was placed onto a piece of weighed filter paper, which was reweighed to determine the amount of material present. The paper was folded to entrap the polymer inside, grasped with a hemostat, and immersed in the 50-ml buffer bath containing the preconstricted aortic ring. As illustrated in FIG. 2, a piece of polymer weighing approximately 0.4 mg induced 30% relaxation in the ring, while 2.1 mg induced 80% relaxation. The data demonstrate that there was a positive response by the organ to the polymer-bound composition of this invention and that the response tended to increase as the dose administered was increased. Thus, the polymer-bound nucleophile/nitric oxide composition has a potent, dose-responsive cardiovascular effect.

The above experiment was repeated with the granular polymer produced in Example 2. A similar effect was observed, though it was less potent because this polymer contained fewer NO-releasing $N_2O_2^-$ groups per gram than the polymer of Example 1.

Figure 3:
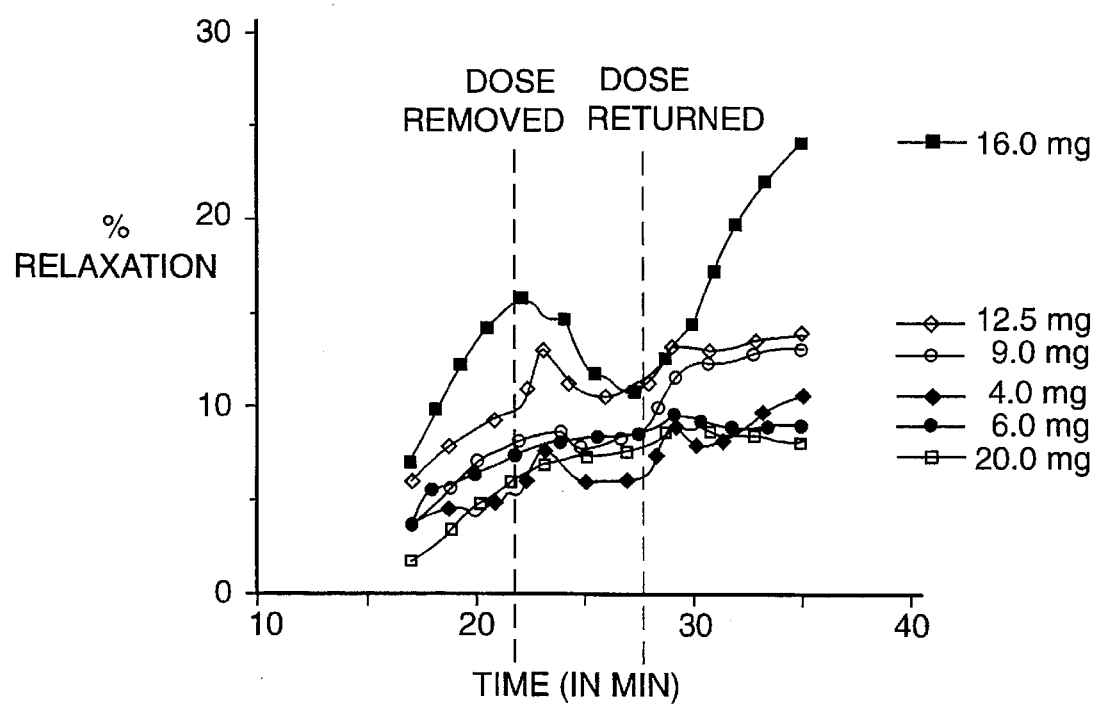
FIG. 3 is a graph illustrating the time course of vascular relaxation with different doses of the polymer-bound nitric oxide-releasing composition of Example 2.

FIG. 3 illustrates the time course of vascular relaxation when different doses of the polymer-bound nitric oxide-releasing composition of Example 2 are first exposed to the aortic ring, causing relaxation, then withdrawn from the organ bath, allowing reconstriction to occur, then reintroduced into the organ bath, causing the vessel to dilate again. In this experiment, a 16-mg sample of the polymer-bound nitric oxide-releasing composition of Example 2 was immersed into the buffer bath. After 15% relaxation had been achieved, the sample was removed from the bath. Upon removal of the polymer-bound composition, the degree of relaxation fell to approximately 11% over about 5 min. The sample of the polymer-bound composition was then returned to the bath, and a doubling of the degree of relaxation to about 25% was observed.

This experiment illustrates that the pharmacological effects of the polymer-bound nitric oxide/nucleophile composition of the present invention can be modulated as desired by controlling the extent and duration of contact between the polymer and the cells or tissues of interest. This feature is particularly advantageous, for example, to localize the effects of nitric oxide release to a specific target organ or situs.

Example 6

This example describes the effect of DETA/NO on DNA synthesis in A375 cells.

Quiescent A375 human melanoma cells were treated with DETA/NO or DETA (20–500 µM) in Dulbecco's Modified Eagle's Medium (DMEM) +10% fetal calf serum (FCS) for 22 hrs. DETA/NO is a NONOate that releases nitric oxide with a 20-hr half-life at 37° C. and pH 7.4. Cells were then pulse-labeled with 1 mCi [$^3$H]thymidine for two hrs. Radioactivity was precipitated with trichloroacetic acid (TCA), recovered, and counted in accordance with methods well-known in the art.

Figure 4A:
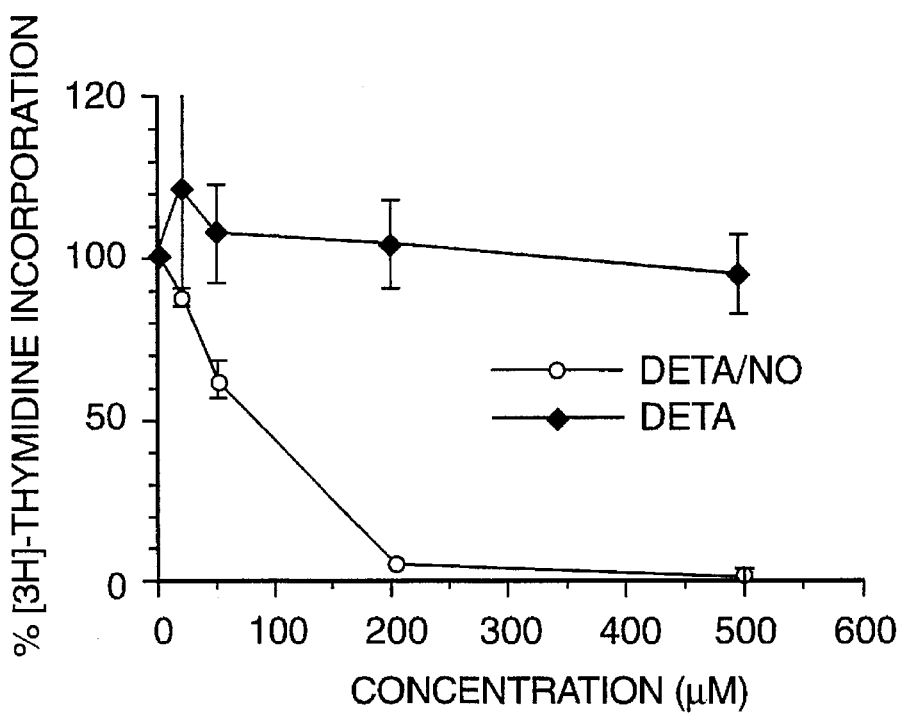
FIG. 4A is a graph of % [$^3$H]thymidine incorporation versus concentration (μM) for A375 human melanoma cells (A375 cells) treated with $(H_2NCH_2CH_2)_2NH$ (DETA) and DETA●2NO (DETA/NO).
Figure 4B:
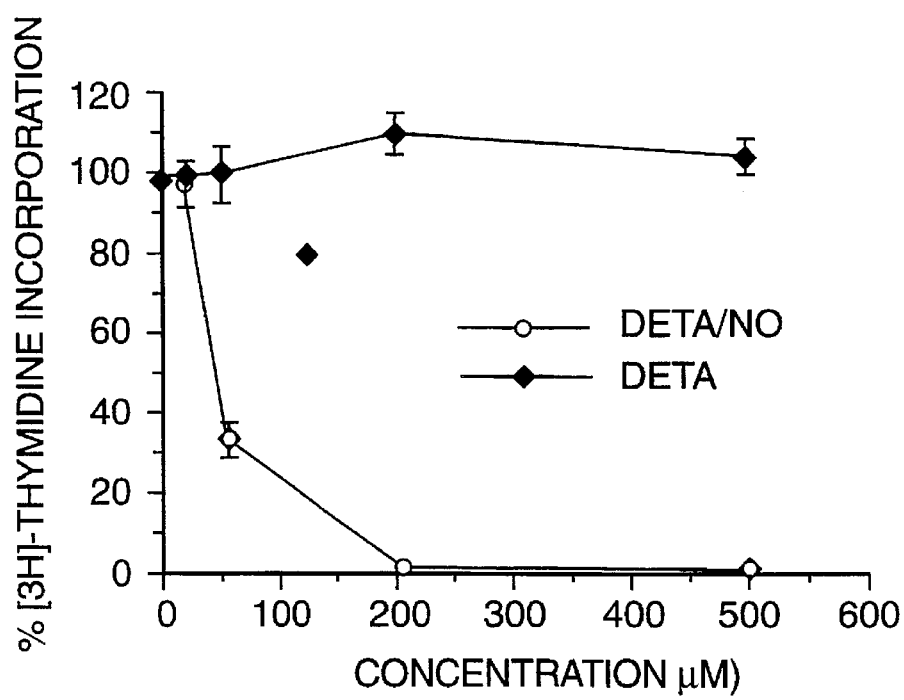
FIG. 4B is a graph of % [$^3$H]thymidine incorporation versus concentration (μM) for rat aorta smooth muscle cells (RA-SM cells) treated with DETA and DETA/NO.

FIGS. 4A and 4B are graphs of % [$^3$H]thymidine incorporation versus concentration (µM) for A375 and RA-SM cells, respectively, treated with DETA (●) and DETA/NO (□). Tritiated thymidine incorporation is expressed as percent of control (DMEM+10% FCS)±1 S. D., where n=3.

As shown in FIGS. 4A and 4B, DETA did not inhibit DNA synthesis in either A375 and RA-SM cells. By contrast, DETA/NO did inhibit DNA synthesis in both A375 and RA-SM cells, with an $IC_{50}$ of about 50–100 µM and 20–50 µM, respectively. These results demonstrate that monomers analogous to the nitric oxide/nucleophile adducts employed in the polymeric compositions used in the methods and nitric-oxide-delivery means of the present invention inhibit cellular DNA synthesis.

Example 7

This example describes the effect of DETA/NO on proliferation of rat aorta smooth muscle (RA-SM) cells.

RA-SM cells in DMEM+10% FCS were seeded at a concentration of 40,000 cells/well in a 24-well culture plate and were allowed to attach to the plate overnight. Cells were then not treated or treated over a seven-day period with 500 µM DETA/NO or DETA on day 1, days 1 and 3, or days 1, 3, and 5. Cells were harvested using trypsin: EDTA on days 1, 3, 5, and 7 and counted using a hemocytometer.

Figure 5A:
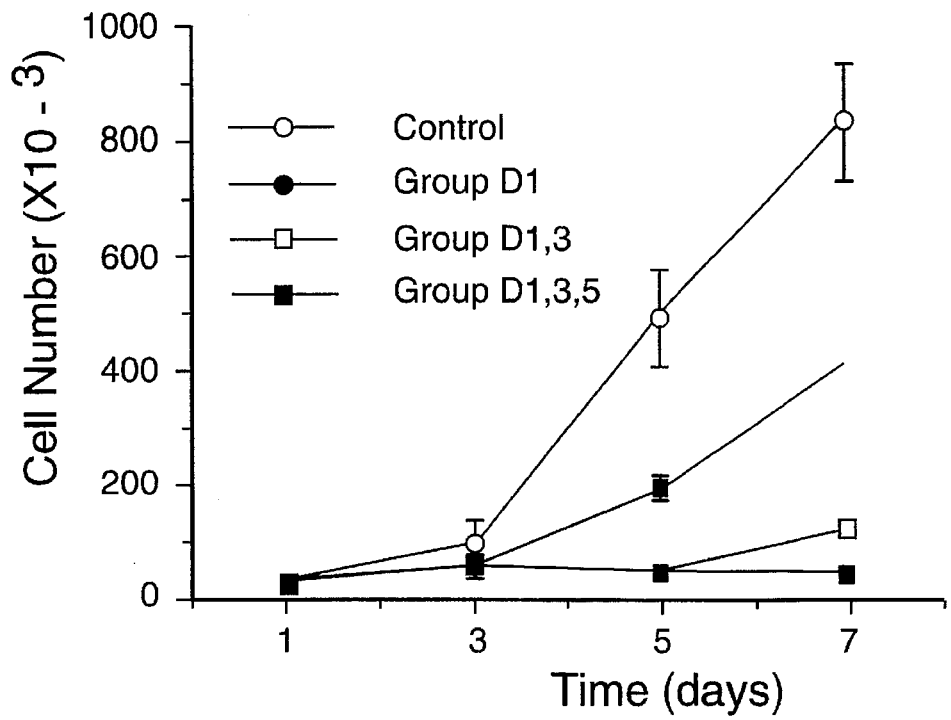
FIG. 5A is a graph of cell number ($\times 10^{-3}$) versus time (days) for RA-SM cells not treated or treated over a seven-day period with DETA/NO on day 1, days 1 and 3, or days 1, 3, and 5.
Figure 5B:
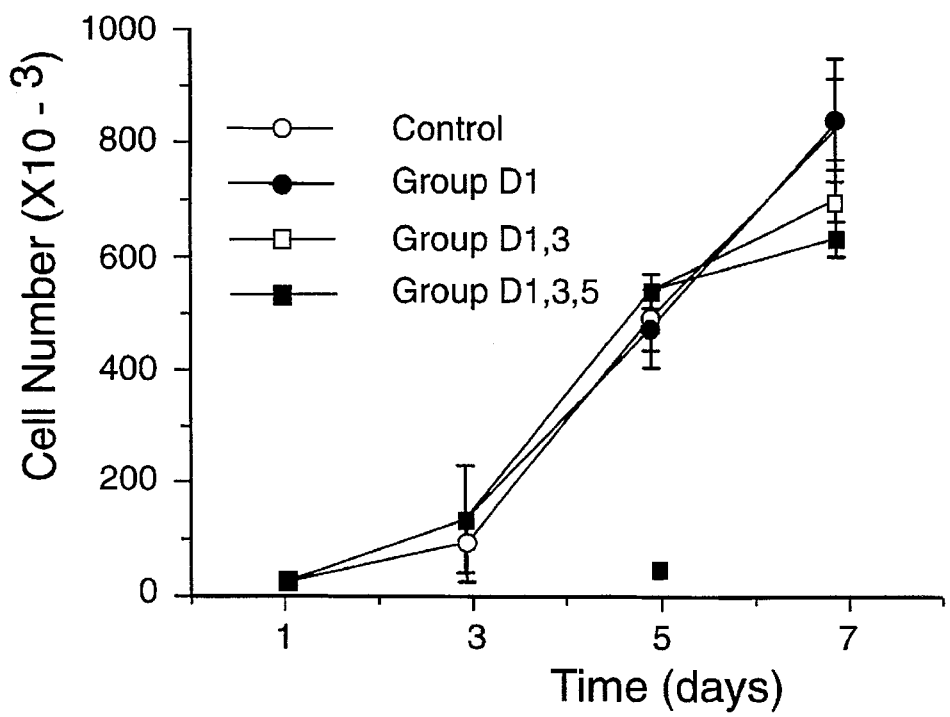
FIG. 5B is a graph of cell number ($\times 10^{-3}$) versus time (days) for RA-SM cells not treated or treated over a seven-day period with DETA on day 1, days 1 and 3, or days 1, 3, and 5.

FIGS. 5A and 5B are graphs of cell number (×10$^{-3}$) versus time (days) for RA-SM cells not treated (○) or treated over a seven-day period with DETA/NO or DETA, respectively, on day 1 (●), days 1 and 3 (□), or days 1, 3, and 5 (■). Cell proliferation is expressed as cell number±1 S. D., where n=3.

As shown in FIG. 5A and 5B, DETA had no effect on RA-SM cell proliferation. By contrast, DETA/NO inhibited RA-SM cell proliferation. A single dose of DETA/NO on day 1 resulted in a cell number on day 7 that was only about half that of the untreated control cells. Exposure of cells to doses of DETA/NO on days 1 and 3 led to an order of magnitude difference in the growth curves of the treated and untreated cells. Exposure of cells to doses of DETA/NO on days 1, 3 and 5 resulted in virtually complete suppression of RA-SM cell proliferation. However, removal of DETA/NO resulted in renewed cell proliferation. Accordingly, these results indicate that the continued presence of the NONOate is required in order to maintain inhibition of smooth muscle cell proliferation; thus, growth of the cells was not irreversibly inhibited, but resumed when the NO source was removed.

Example 8

This example describes the effects of DEA/NO, SPER/NO, NaNp, and ASA on platelet aggregation in rabbits.

Anesthetized rabbits were treated with 50 nmol/kg DEA/NO ($Et_2N[N(O)NO]Na$), NaNp or ASA, or 500 nmol/kg SPER/NO, or 25 mg ASA, which is approximately 50,000 nmol/kg by intravenous bolus injection.

Figure 6:
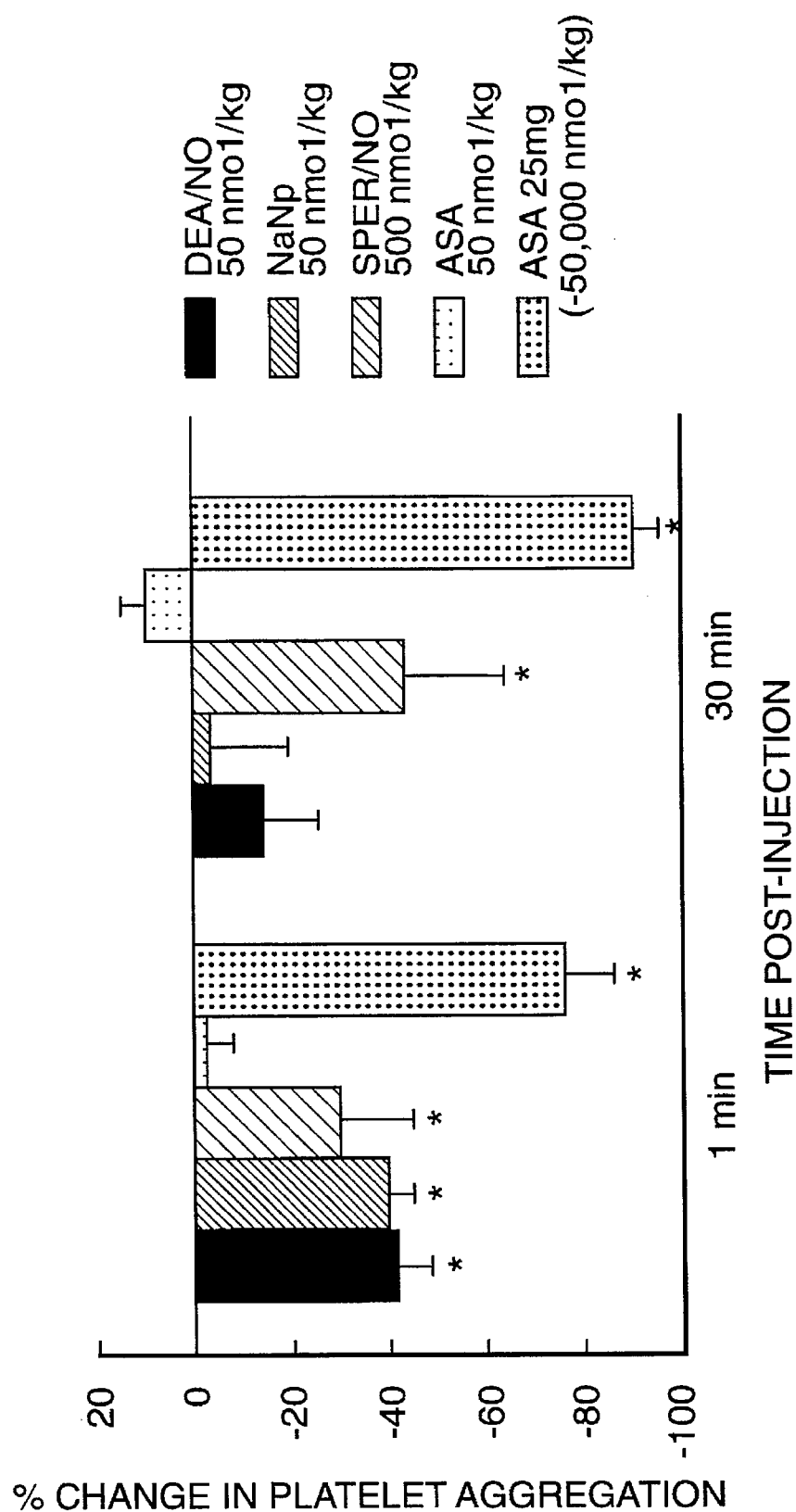
FIG. 6 is a bar graph of % change in platelet aggregation in rabbits versus time post-injection (1 min or 30 min) with $Et_2N[N(O)NO]Na$ (DEA/NO), spermine●2NO (SPER/NO), sodium nitroprusside (NaNp), or aspirin (ASA).

FIG. 6 is a bar graph of % change in platelet aggregation in rabbits versus time post-injection (1 min or 30 min) with DEA/NO, SPER/NO, NaNp or ASA. Percent inhibition of platelet aggregation was determined by impedance aggregometry on whole blood withdrawn 1 min or 30 min after intravenous administration of a dose of a drug as indicated. Collagen was used as the aggregating agent. Values given are means±SEM, where n=2–6. Values marked with an asterisk (*) are significantly different ($p<0.05$) from those observed for untreated control blood.

As shown in FIG. 6, 50 nmol/kg DEA/NO, 50 nmmol/kg NaNp, 500 nmol/kg SPER/NO, and 25 mg ASA significantly inhibited platelet aggregation at 1 min post-injection, whereas only 500 nmol/kg SPER/NO and 25 mg ASA significantly inhibited platelet aggregation at 30 min post-injection. The magnitude and duration of the antiplatelet effects of DEA/NO and SPER/NO correlate with their spontaneous nitric oxide release rates in aqueous solution (Diodati et al., *Thrombosis and Haemostasis*, 70, 654–658 (1993)).

Example 9

This example describes the effects of DEA/NO, NaNp and SPER/NO on blood pressure in rabbits.

Anesthetized New Zealand white rabbits were treated with 50 nmol/kg DEA/NO, 500 nmol/kg SPER/NO or 50 nmol/kg NaNp by intravenous injection.

Figure 7:
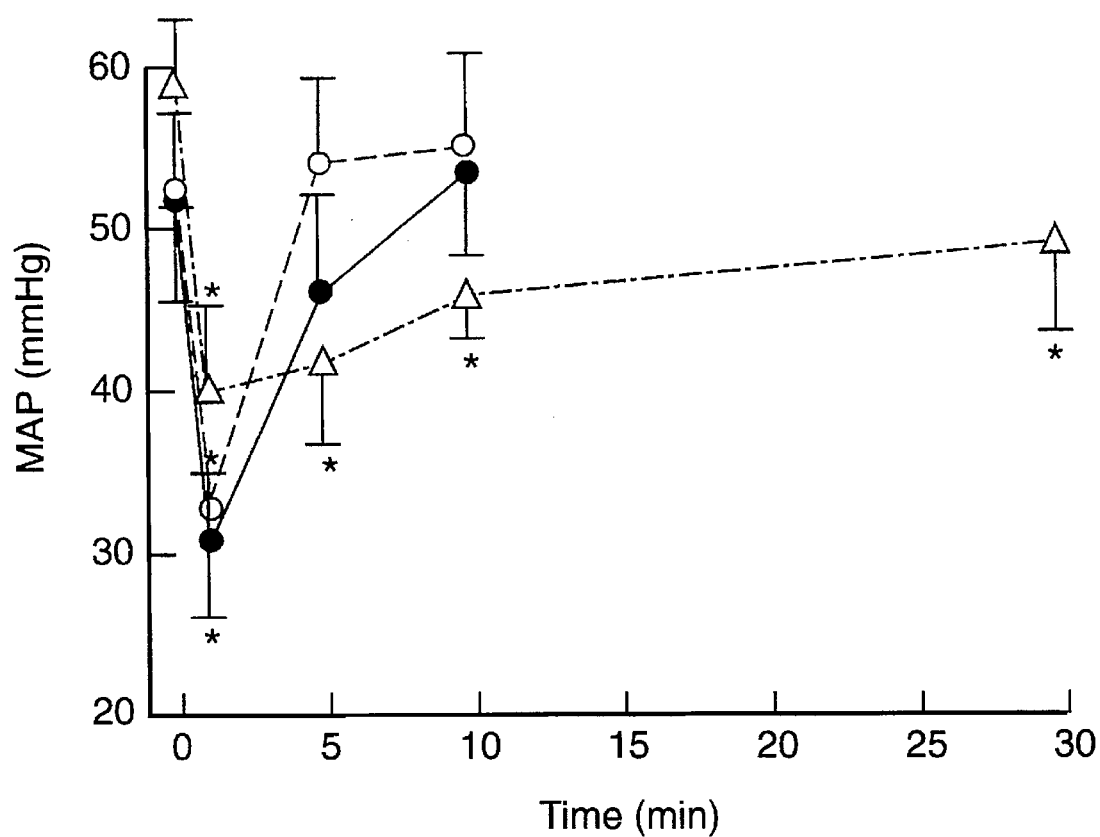
FIG. 7 is a graph of mean arterial pressure (MAP) in rabbits versus time (min) after intravenous injection with DEA/NO, SPER/NO, or NaNp.

FIG. 7 is a graph of mean arterial pressure (MAP) in rabbits versus time (min) after intravenous injection with 50 nmol/kg DEA/NO (●), 500 nmol/kg SPER/NO (▲), or 50 nmol/kg NaNp (○). Values given are means±S.D. MAP readings marked with an asterisk differ significantly ($p<0.05$) from pre-injection values.

As shown in FIG. 7, 50 nmol/kg DEA/NO, 500 nmol/kg SPER/NO, and 50 nmol/kg NaNp all significantly reduced MAP within the first couple of minutes after administration. However, only 500 nmol/kg SPER/NO was effective in reducing MAP over the course of 30 min post-injection (Diodati et al., *J. Cardiovasc. Pharmacol.*, 22, 287–292 (1993)). DEA/NO is a short-acting vasodilator, whereas SPER/NO is a longer-acting vasodilator, demonstrating significant hypotensive effects 30 min after injection.

Example 10

This example describes the effects of MAHMA/NO on platelet-dependent thrombosis in baboons.

An ex vivo arteriovenous shunt was established in baboons by cannulating the femoral artery and vein and connecting them with a length of tubing. The tubing was split in the middle and a drug infusion device was inserted. Downstream from the drug infusion device, a highly thrombogenic surface, e.g., a polyester graft, was inserted. Baboon blood platelets were made radioactive using $^{111}$Indium. Platelet accumulation on the polyester graft portion of the AV shunt was monitored for about one hour by measuring the increase in radioactivity with a gamma radiation counter. Increases in radioactivity indicate increases in platelet deposition on the polyester graft.

MAHMA/NO was infused through the porous wall of the drug infusion device so that it entered the blood stream in the slowest moving blood layers at the graft-blood interface, i.e., around the inside surface of the wall of the shunt. As the drug moved downstream, it reached concentrations along the vessel wall that are about 200 times those achieved by infusing drug uniformly into the blood flow field. Drugs which prevent thrombosis result in fewer platelets being deposited on the polyester graft.

Figure 8:
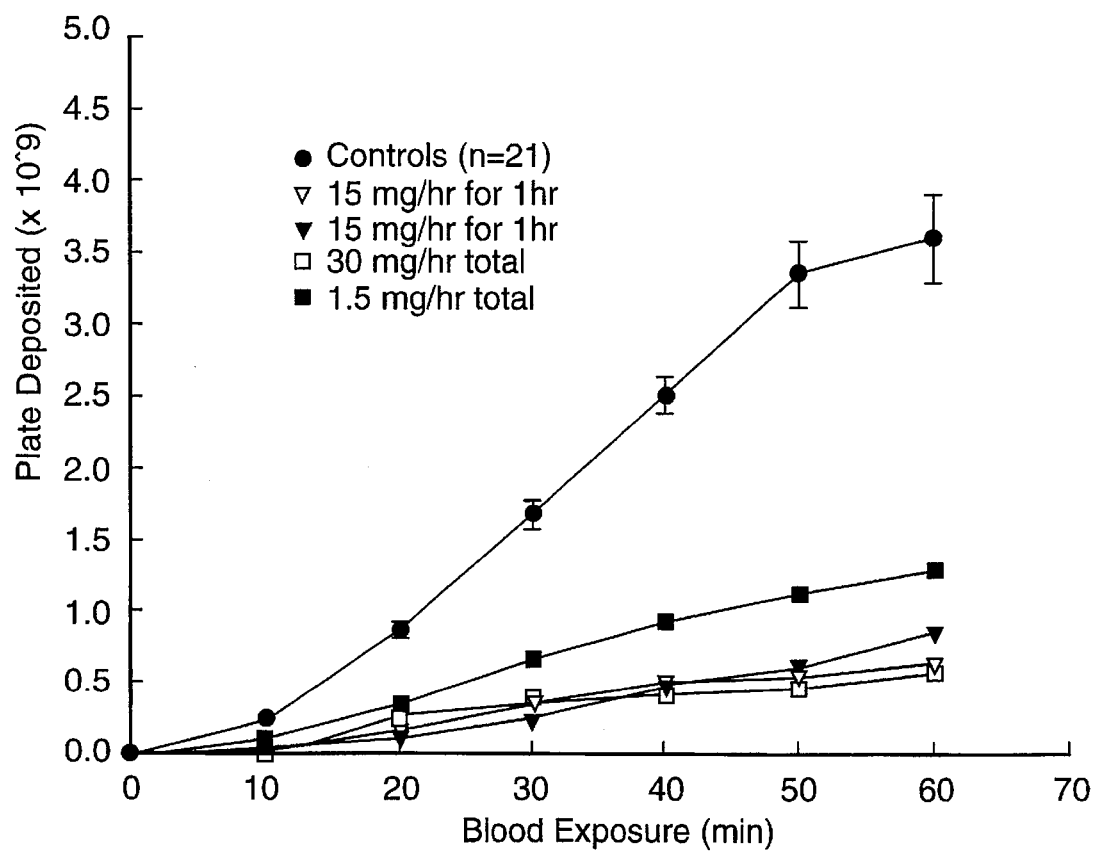

FIG. 8 is a graph of platelets deposited ($\times 10^{-9}$) versus blood exposure (min) to MAHMA/NO. FIG. 8 shows that, at high doses of MAHMA/NO, platelet deposition on the polyester graft was virtually eliminated. These results demonstrate that the localized administration of NONOates inhibits platelet adhesion and aggregation associated with thrombosis.

Given that 0.05 mg/hr of MAHMA/NO reduces platelet deposition at the graft by half, a graft coated with a nitric oxide-releasing polymer, for example, that releases NO at a rate of 0.5 μmol/hr would be expected to similarly be useful to reduce platelet deposition.

Example 11

This example describes how a pharmaceutical composition comprising a NONOate may be prepared for intravenous or intraperitoneal injection and how it may be administered.

A stock solution of NO complex is prepared by weighing an appropriate amount of an NO complex into a volumetric flask. For example, for a $10^{-2}$M solution, 15.5 mg of DEA/NO is weighed into a 10 ml volumetric flask. Ice-cold 10 mM NaOH is added to bring the volume to 10 ml. From this stock solution, a dosing solution is prepared with an excess of phosphate-buffered saline (PBS), pH 7.4. For example, to prepare a $10^{-6}$M dosing solution, 10 μl of $10^{-2}$M stock solution is diluted 1:10,000, i.e., to 10 ml with ice-cold PBS. This dosing solution is then used to provide a single dose or a continuous infusion to mammals, e.g., continuous infusion 1–2 μg/kg/min for 5 minutes to lambs or a single daily intravenous injection of 10 μg/kg to pigs.

Example 12

This example describes how a pharmaceutical composition comprising an NO adduct may be prepared for transdermal administration and how it may be administered.

An NO adduct is dissolved in enough ice-cold 10% distilled water in propylene glycol to provide the proper dosing concentration, e.g., 5 μmol. 0.2 ml of the solution is applied to a shaved area of skin three times per week. Alternatively, the NO adduct is dissolved in ice-cold distilled water and then diluted 10-fold with cold propylene glycol and applied as before.

Example 13

This example describes how a balloon catheter comprising an NO adduct may be prepared and used to administer NO at the site of angioplasty.

An NO adduct is dissolved in water and maintained ice-cold. A balloon catheter is constructed from a microporous membrane, e.g., 150 Å polycarbonate membrane (Nucleopore®, Costar Corporation, Cambridge, Mass. or Fluoropore®, Millipore Corporation, Bedford, Mass.), and inserted into the blood vessel at the site of angioplasty. The NO adduct solution is used to inflate the balloon at the site of injury. An electrical current (e.g., 5 mA, 8–10 V) is passed through the balloon for 1–2 minutes. During this time, 100–300 µg NO of adduct is expected to be transferred through the balloon into the vessel wall.

Example 14

This example describes how a biodegradable polymer comprising an NO adduct may be prepared and used to administer NO to an injured blood vessel.

In small increments with gentle stirring, polyoxypropylene-polyoxyethylene block co-polymer (Pluronic® F127 NF, BASF Corporation, Parsippany, N.J.) is added to ice-cold water or phosphate-buffered saline, pH 7.4, to make a 25% by weight solution. The appropriate amount of NO adduct to provide the needed dosage is contained in the water or PBS. This results in a clear solution, a portion of which, e.g., 0.2 ml, is added to the outside of an injured vessel, e.g., to a balloon-injured rat carotid artery, just prior to closing the wound. The resulting gel is expected to deliver the NO over a period of several hours to a few days.

Example 15

This example describes how a biodegradable polymer comprising an NO adduct may be prepared in situ for release of NO at a site of blood vessel injury.

In N-methyl-2-pyrrolidone containing the requisite amount of NO adduct, ATRIGEL™ (ATRIX Laboratories, Fort Collins, Colo.) is dissolved by stirring to result in a 50% solution of polymer by weight. Polymers which can be used include, e.g., poly(DL-lactide); 75/25 poly(DL-lactide-co-glycolide); and 50/50 poly(DL-lactide-co-caprolactone). The resulting solution gels when it comes into contact with water, e.g., in a body cavity. A portion of this solution, e.g., 0.2 ml, is injected around the area of vessel injury. After the solution gels, the drug is eluted from this system over a period of days or weeks, depending on the polymer system used.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method for the prophylaxis of restenosis and related disorders in a mammal, which method comprises the administration of nitric oxide by a nitric oxide delivery means, said delivery means comprising a prophylactically effective amount of a nitric oxide-releasing agent, said agent selected from the group consisting of a compound comprising a nitric oxide-releasing $N_2O_2^-$ functional group and a polymer matrix into which has been incorporated a nitric oxide-releasing $N_2O_2^-$ functional group, said agent being capable of locally releasing nitric oxide to a site at risk for restenosis in said mammal.

2. The method of claim 1 wherein
M$^{+x}$ is a pharmaceutically acceptable cation, where x is the valence of the cation, a is 1 or 2, and b and c are the smallest integers that result in a neutral compound.

3. The method of claim 2 wherein J is a moiety which is linked to the nitrogen of the remainder of the compound through an atom other than a carbon atom.

4. The method of claim 2 wherein the nitric oxide releasing compound is a compound other than a salt of alanosine or dopastin.

5. The method of claim 1 wherein said nitric oxide-releasing $N_2O_2^-$ functional group is contained in a compound of the formula:

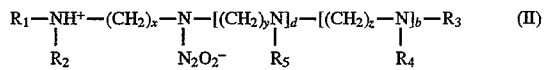

wherein b and d are the same or different and are zero or one, $R_1$, $R_2$, $R_3$, $R_4$, and $R_5$ are the same or different and are hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12.

6. The method of claim 1 wherein said nitric oxide-releasing $N_2O_2^-$ functional group is contained in a compound of the formula:

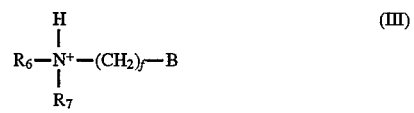

wherein B is

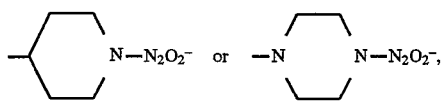

$R_6$ and $R_7$ are the same or different and are hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

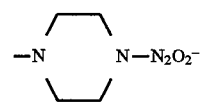

then f is an integer from 2 to 12.

7. The method of claim 6 wherein B is the substituted piperazine moiety.

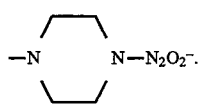

8. The method of claim 1 wherein said nitric oxide-releasing $N_2O_2^-$ functional group is contained in a compound of the formula:

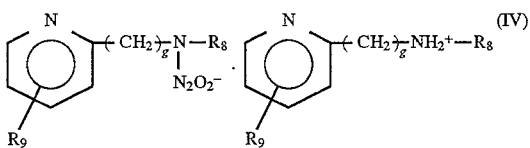 (IV)

wherein $R_8$ is hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$-$C_{12}$ straight or branched chain alkyl, and g is an integer from 2 to 6.

9. The method of claim 1 wherein said nitric oxide-releasing $N_2O_2^-$ functional group is contained in a compound of the formula:

 (V)

wherein $R_1$ and $R_2$ are independently selected from the group consisting of a $C_{1-12}$ straight or branched chain alkyl and benzyl, $M^{+x}$ is a pharmaceutically acceptable cation, and x is the valence of the cation.

10. The method of claim 9 wherein $R_1$ and $R_2$ are selected so that $R_1$ and $R_2$ are unbranched on the alpha carbon atom or $R_1$ and $R_2$, together with the nitrogen atom to which they are bonded, form a heterocyclic group.

11. The method of claim 10 wherein the heterocyclic group is selected from the group consisting of pyrrolidino, piperidino, piperazino and morpholino.

12. The method of claim 1 wherein said nitric oxide-releasing $N_2O_2^-$ functional group is contained in a compound of the formula:

$$K[(M)_x{'}(L)_y(R^1R^2N-N_2O_2)_z]$$ (VI)

wherein M is a pharmaceutically acceptable metal, or where x is at least two, a mixture of two different pharmaceutically acceptable metals, L is a ligand different from ($R^1R^2N-N_2O_2$) and is bound to at least one metal, $R^1$ and $R^2$ are each organic moieties and are the same or different, x is an integer from 1 to 10, x' is the formal oxidation state of the metal M, and is an integer from 1 to 6, y is an integer from 1 to 18, with the proviso that when y is at least 2, the ligands L are the same or different, z is an integer from 1 to 20, and K is a pharmaceutically acceptable counterion to render the compound neutral to the extent necessary.

13. The method of claim 12 wherein when M is copper, x is one L is methanol, and y is one, then at least one of $R^1$ or $R^2$ is a moiety other than ethyl.

14. The method of claim 1 wherein said nitric oxide-releasing $N_2O_2^-$ functional group is contained in a compound of the formula:

$$[R-N(H)N(NO)O-]_yX$$ (VII)

wherein R is a $C_{2-8}$ lower alkyl, phenyl, benzyl, or a $C_{3-8}$ cycloalkyl, any of which R groups can be substituted by one to three substituents, which are the same or different and are selected from the group consisting of halo, hydroxy, a $C_{1-8}$ alkoxy, $-NH_2$, $-C(O)NH_2$, $-CH(O)$, $-C(O)OH$, and $-NO_2$, X is a pharmaceutically acceptable cation, a pharmaceutically acceptable metal center, or a pharmaceutically acceptable organic group selected from the group consisting of a $C_{1-8}$ lower alkyl, $-C(O)$ $CH_3$, and $-C(O)NH_2$, and y is an integer from 1 to 3, consistent with the valence of X.

15. The method of claim 1 wherein said nitric oxide-releasing $N_2O_2^-$ functional group is contained in a compound of the formula:

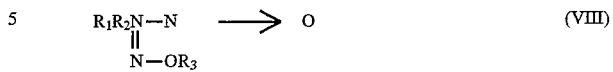 (VIII)

wherein $R_1$ and $R_2$ are independently chosen from a $C_{1-12}$ straight chain alkyl, a $C_{1-12}$ alkoxy or acyloxy substituted straight chain alkyl, a $C_{2-12}$ hydroxy or halo substituted straight chain alkyl, a $C_{3-12}$ branched chain alkyl, a $C_{3-12}$ hydroxy, halo, alkoxy, or acyloxy substituted branched chain alkyl, a $C_{3-12}$ straight or branched chain olefinic unsubstituted or substituted with hydroxy, alkoxy, acyloxy, halo or benzyl, or $R_1$ and $R_2$ together with the nitrogen atom to which they are bonded form a heterocyclic group, and $R_3$ is a group selected from a $C_{1-12}$ straight chain and a $C_{3-12}$ branched chain alkyl which are unsubstituted or substituted by hydroxy, halo, acyloxy or alkoxy, a $C_{2-12}$ straight chain or a $C_{3-12}$ branched chain olefinic which are unsubstituted or substituted by halo, alkoxy, acyloxy or hydroxy, a $C_{1-12}$ unsubstituted or substituted acyl, sulfonyl, and carboxamido; or $R_3$ is a group of the formula $-(CH_2)_n-ON=N(O)NR_1R_2$, wherein n is an integer of 2–8, and $R_1$ and $R_2$ are as defined above.

16. The method of claim 15 wherein $R_1$, $R_2$ and $R_3$ contain a moiety other than a halo or a hydroxy substituent α to a heteroatom.

17. The method of claim 15 wherein the heterocyclic group is selected from the group consisting of pyrrolidino, piperidino, piperazino, and morpholino.

18. The method of claim 1 wherein said polymer is selected from the group consisting of polyolefins, polyethylenimine and derivatives thereof, polyethers, polyesters, polyamides, polyurethanes, colestipol and derivatives thereof.

19. The method of claim 1 wherein said polymer is biodegradable.

20. A method for the treatment of restenosis in a mammal, which method comprises the administration of nitric oxide by a nitric oxide delivery means, said delivery means comprising an effective treatment amount of a nitric oxide-releasing agent, said agent selected from the group consisting of (i) a compound comprising a nitric oxide-releasing $N_2O_2^-$ functional group wherein said compounds is of the formula I, II, III, IV, V, VI, VII or VIII, or (ii) a polymer in admixture with a compound comprising a nitric oxide-releasing $N_2O_2^-$ functional group and having the formula I, II, III, IV, V, VI, VII or VIII, or (iii) a polymer comprising a polymeric backbone, wherein said polymeric backbone is selected from the group consisting of a polyolefin, a polyether, a polyester, a polyamide, polyethyleneimine, a polyurethane, colestipol, a peptide, a starburst dendrimer, a protein, and at least one nitric oxide-releasing functional group selected from the group consisting of X-[B(O)NO] or [N(O)NO]X wherein X is an organic moiety covalently bonded to said group, and wherein said group is covalently bonded is said polymer through said organic moiety X, wherein in the compound of said formula I, J is an inorganic moiety or an organic moiety selected from the group consisting of $C_1$-$C_{12}$ aliphatic, $C_3$-$C_8$ cycloalkyl, benzyl, phenyl, substituted benzyl, substituted phenyl, benzylcarbonyl, phenylcarbonyl, substituted benzylcarbonyl, substituted phenylcarbonyl, $C_1$-$C_{12}$ acyl, and

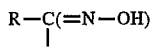

wherein R is $C_1$–$C_{12}$ aliphatic, $C_3$–$C_8$ cycloalkyl, benzyl, phenyl, substituted benzyl or substituted phenyl, and said substituted benzyl and substituted phenyl is substituted with one or two substituents selected from the group consisting of halogen, hydroxy, $C_1$–$C_4$ alkyl, $C_1$–$C_4$ alkoxy, amino, mono $C_1$–$C_4$ alkylamino, di $C_1$–$C_4$ alkyl-amino, phenyl and phenoxy, said agent being capable of locally releasing nitric oxide to a site affected by restenosis in said mammal.

21. The method of claim 20 wherein said nitric oxide-releasing $N_2O_2^-$ functional group is contained in a compound of the formula:

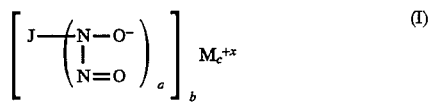

wherein J is an organic or inorganic moiety, $M^{+x}$ is a pharmaceutically acceptable cation, where x is the valence of the cation, a is 1 or 2, and b and c are the smallest integers that result in a neutral compound.

22. The method of claim 21 wherein J is a moiety which is linked to the nitrogen of the remainder of the compound through an atom other than a carbon atom.

23. The method of claim 21 wherein the compound is a compound other than a salt of alanosine or dopastin.

24. The method of claim 20 wherein said nitric oxide-releasing $N_2O_2^-$ functional group is contained in a compound of the formula:

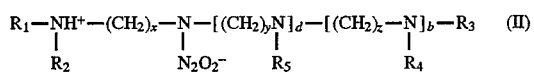

wherein b and d are the same or different and are zero or one, $R_1$, $R_2$, $R_3$, $R_4$, and $R_5$ are the same or different and are hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12.

25. The method of claim 20 wherein said nitric oxide-releasing $N_2O_2^-$ functional group is contained in a compound of the formula:

wherein B is

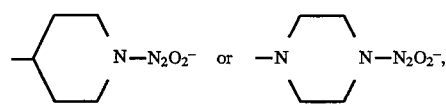

$R_6$ and $R_7$ are the same or different and are hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and f is an integer from 0 to 12.

26. The method of claim 25 wherein B is the substituted piperazine moiety.

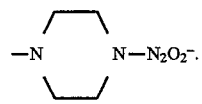

27. The method of claim 20 wherein said nitric oxide-releasing $N_2O_2^-$ functional group is contained in a compound of the formula:

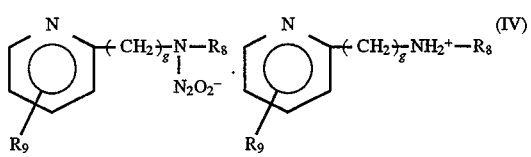

wherein $R_8$ is hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$–$C_{12}$ straight or branched chain alkyl, and g is an integer from 2 to 6.

28. The method of claim 20 wherein said nitric oxide-releasing $N_2O_2^-$ functional group is contained in a compound of the formula:

wherein $R_1$ and $R_2$ are independently selected from the group consisting of a $C_{1-12}$ straight or branched chain alkyl and benzyl, $M^{+x}$ is pharmaceutically acceptable cation, and x is the valence of the cation.

29. The method of claim 28 wherein $R_1$ and $R_2$ are selected so that $R_1$ and $R_2$ are unbranched on the alpha carbon atom or $R_1$ and $R_2$, together with the nitrogen atom to which they are bonded, form a heterocyclic group.

30. The method of claim 29 wherein the heterocyclic group is selected from the group consisting of pyrrolidino, piperidino, piperazino and morpholino.

31. The method of claim 20 wherein said nitric oxide-releasing $N_2O_2^-$ functional group is contained in a compound of the formula:

wherein M is a pharmaceutically acceptable metal, or where x is at least two, a mixture of two different pharmaceutically acceptable metals, L is a ligand different from ($R^1R^2N$—$N_2O_2$) and is bound to at least one metal, $R^1$ and $R^2$ are each organic moieties and are the same or different, x is an integer from 1 to 10, x' is the formal oxidation state of the metal M, and is an integer from 1 to 6, y is an integer from 1 to 18, with the proviso that when y is at least 2, the ligands L are the same or different, z is an integer from 1 to 20, and K is a pharmaceutically acceptable counterion to render the compound neutral to the extent necessary.

32. The method of claim 31 wherein when M is copper, x is one, L is methanol, and y is one, then at least one $R^1$ or $R^2$ is moiety other than ethyl.

33. The method of claim 20 wherein said nitric oxide-releasing $N_2O_2^-$ functional group is contained in a compound of the formula:

wherein R is a $C_{2-8}$ lower alkyl, phenyl, benzyl, or a $C_{3-8}$ cycloalkyl, any of which R groups can be substituted by one to three substituents, which are the same or different and are selected from the group consisting of halo, hydroxy, $C_{1-8}$ alkoxy, —$NH_2$, —$C(O)NH_2$, —$CH(O)$, —$C(O)OH$, and —$NO_2$, X is a pharmaceutically acceptable cation, a pharmaceutically acceptable metal center, or a pharmaceutically acceptable organic group selected from the group consisting of a $C_{1-8}$ lower alkyl, —$C(O)CH_3$, and —$C(O)NH_2$, and y is an integer from 1 to 3, consistent with the valence of X.

34. The method of claim 20 wherein said nitric oxide-releasing $N_2O_2^-$ functional group is contained in a compound of the formula:

wherein $R_1$ and $R_2$ are independently chosen from a $C_{1-12}$ straight chain alkyl, a $C_{1-12}$ alkoxy or acyloxy substituted straight chain alkyl, a $C_{2-12}$ hydroxy or halo substituted straight chain alkyl, a $C_{3-12}$ branched chain alkyl, a $C_{3-12}$ hydroxy, halo, alkoxy, or acyloxy substituted branched chain alkyl, a $C_{3-12}$ straight or branched chain olefinic unsubstituted or substituted with hydroxy, alkoxy, acyloxy, halo or benzyl, or $R_1$ and $R_2$ together with the nitrogen atom to which they are bonded form a heterocyclic group, and $R_3$ is a group selected from a $C_{1-12}$ straight chain and a $C_{3-12}$ branched chain alkyl which are unsubstituted or substituted by hydroxy, halo, acyloxy or alkoxy, a $C_{2-12}$ straight chain or a $C_{3-12}$ branched chain olefinic which are unsubstituted or substituted by halo, alkoxy, acyloxy or hydroxy, a $C_{1-12}$ unsubstituted or substituted acyl, sulfonyl, and carboxamido; or $R_3$ is a group of the formula —$(CH_2)_n$—$ON=N(O)NR_1R_2$, wherein n is an integer of 2–8, and $R_1$ and $R_2$ are as defined above.

35. The method of claim 34 wherein $R_1$, $R_2$ and $R_3$ contain a moiety other than a halo or a hydroxy substituent α to a heteroatom.

36. The method of claim 34 wherein the heterocyclic group is selected from the group consisting of pyrrolidino, piperidino, piperazino and morpholino.

37. The method of claim 20 wherein said polymer is selected from the group consisting of polyolefins, polyethylenimine and derivatives thereof, polyethers, polyesters, polyamides, polyurethanes, colestipol and derivatives thereof.

38. The method of claim 20 wherein said polymer is biodegradable.

39. A method for the prophylaxis of restenosis in a mammal, which method comprises the administration of a prophylactically effective amount of a nitric oxide-releasing agent, said agent selected from the group consisting of (i) a compound comprising a nitric oxide-releasing $N_2O_2^-$ functional group wherein said compound is of the formula I, II, III, IV, V, VI, VII or VIII, or (ii) a polymer in admixture with a compound comprising a nitric oxide-releasing $N_2O_2^-$ functional group and having the formula I, II, III, IV, V, VI, VII or VIII, or (iii) a polymer comprising a polymeric backbone, wherein said polymeric backbone is selected from the group consisting of a polyolefin, a polyether, a polyester, a polyamide, polyethyleneimine, a polyurethane, colestipol, a peptide, a starburst dendrimer, a protein, and at least one nitric oxide-releasing functional group selected from the group consisting of X—[N(O)NO] or [N(O)NO]—X wherein X is an organic moiety covalently bonded to said group, and wherein said group is covalently bonded in said polymer through said organic moiety X, wherein in the compound of said formula I, J is an inorganic moiety or an organic moiety selected from the group consisting of $C_1$–$C_{12}$ aliphatic, $C_3$–$C_8$ cycloalkyl, benzyl, phenyl, substituted benzyl, substituted phenyl, benzylcarbonyl, phenycarbonyl, substituted benzylcarbonyl, substituted phenylcarbonyl, $C_1$–$C_{12}$ acyl, and

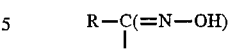

wherein R is $C_1$–$C_{12}$ aliphatic, $C_3$–$C_8$ cycloalkyl, benzyl, phenyl, substituted benzyl or substituted phenyl, and said substituted benzyl and substituted phenyl is substituted with one or two substituents selected from the group consisting of halogen, hydroxy, $C_1$–$C_4$ alkyl, $C_1$–$C_4$ alkoxy, amino, mono $C_1$–$C_4$ alkylamino, di $C_1$–$C_4$ alkyl-amino, phenyl and phenoxy, said agent being capable of locally releasing nitric oxide to a site at risk for restenosis in said mammal.

40. A method for the therapeutic treatment of restenosis in a mammal, which method comprises the administration of a therapeutically effective amount of a nitric oxide-releasing agent, said agent selected from the group consisting of (i) a compound comprising a nitric oxide-releasing $N_2O_2^-$ functional group wherein said compound is of the formula I II, III, IV, V, VI, VII or VIII, or (ii) a polymer in admixture with a compound comprising a nitric oxide-releasing $N_2O_2^-$ functional group and having the formula I, II, III, IV, V, VI, VII or VIII, or (iii) a polymer comprising a polymeric backbone, wherein said polymeric backbone is selected from the group consisting of a polyolefin, a polyether, a polyester, polyamide, polyethyleneimine, a polyurethane, colestipol, a peptide, a starburst dendrimer, a protein, and at least one nitric oxide-releasing functional group selected from the group consisting of X—[N(O)NO] or [N(O)NO]—X wherein X is an organic moiety covalently bonded to said group, and wherein said group is covalently bonded in said polymer through said organic moiety X, wherein in the compound of said formula I, J is an inorganic moiety or an organic moiety selected from the group consisting of $C_1$–$C_{12}$ aliphatic, $C_3$–$C_8$ cycloalkyl, benzyl, phenyl, substituted benzyl, substituted phenyl, benzylcarbonyl, phenylcarbonyl, substituted benzylcarbonyl, substituted phenylcarbonyl, $C_1$–$C_{12}$ acyl, and

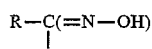

wherein R is $C_1$–$C_{12}$ aliphatic, $C_3$–$C_8$ cycloalkyl, benzyl, phenyl, substituted benzyl or substituted phenyl, and said substituted benzyl and substituted phenyl is substituted with one or two substituents selected from the group consisting of halogen, hydroxy, $C_1$–$C_4$ alkyl, $C_1$–$C_4$ alkoxy, amino, mono $C_1$–$C_4$ alkylamino, di $C_1$–$C_4$ alkyl-amino, phenyl and phenoxy, said agent being capable of locally releasing nitric oxide to a site affected by restenosis in said mammal.

41. The method of claim 18 wherein said polyolefin is selected from the group consisting of polystyrene, polypropylene, polyethylene, polytetrafluorethylene, polyvinylidene , difluoride, and polyvinylchloride; said polyether is polyethyleneglycol; said polyester is poly(lactide/glycolide); and said polyamide is nylon.

42. The method of claim 37 wherein said polyolefin is selected from the group consisting of polystyrene, polypropylene, polyethylene, polytetrafluorethylene, polyvinylidene difluoride, and polyvinylchloride; said polyether is polyethyleneglycol; said polyester is poly(lactide/glycolide); and said polyamide is nylon.

* * * * *